United States Patent [19]

Schwartz

[11] Patent Number: 5,608,112
[45] Date of Patent: Mar. 4, 1997

[54] PROCESS FOR REDUCING ORGANIC POLLUTANTS

[75] Inventor: Jeffrey Schwartz, Princeton, N.J.

[73] Assignee: The Trustees of Princeton University, Princeton, N.J.

[21] Appl. No.: 499,932

[22] Filed: Jul. 10, 1995

Related U.S. Application Data

[63] Continuation-in-part of Ser. No. 211,983, Aug. 15, 1994, Pat. No. 5,608,135.

[51] Int. Cl.$^6$ .............. C07C 209/30; C07C 1/26
[52] U.S. Cl. ............ 564/415; 546/184; 546/192; 546/348; 546/152; 546/164; 548/110; 548/335.1; 548/343.5; 564/416; 564/420; 588/205; 588/221; 588/244; 208/289; 208/290; 208/295; 423/351; 423/364; 210/909; 540/139; 540/145; 544/180; 544/181
[58] Field of Search ............... 588/205, 244, 588/221; 208/289, 290, 295; 423/DIG. 20, 351, 364; 210/909; 564/415, 416, 420; 548/110, 335.1, 343.5; 546/184, 192, 152, 348, 164; 544/180, 181; 540/139, 145

[56] References Cited

U.S. PATENT DOCUMENTS

| | | | |
|---|---|---|---|
| 4,188,346 | 2/1980 | Markley | 570/204 |
| 4,447,667 | 5/1984 | Parker et al. | 588/207 |
| 4,804,779 | 2/1989 | Novinson | 562/542 |
| 4,931,167 | 6/1990 | Wilwerding | 208/262.5 |
| 4,957,717 | 9/1990 | Imamura et al. | 423/240 |
| 5,004,551 | 4/1991 | Sublette | 210/909 |
| 5,035,784 | 7/1991 | Anderson et al. | 204/158.1 |
| 5,154,836 | 10/1992 | Clough | 210/747 |
| 5,322,547 | 6/1994 | Nagel et al. | 75/414 |
| 5,345,031 | 9/1994 | Schwartz et al. | 588/206 |
| 5,345,032 | 9/1994 | Marks et al. | 588/207 |

OTHER PUBLICATIONS

Bergbreiter et al., *J. Org. Chem.*, 54, 5138–5141, (1989).
Bosin et al., *Tetrahedron Letters*, 4699–4700, (1973).
Carfagna et al., *J. Mol.Cat.* 57 (1989), 23–28.
Dennis et al., *Bulletin of Environmental Contamination and Toxicology*, 22:6, pp. 750–753 (1979).
Hill et al., *Appl. Biochem. Biotechnol.*, 20–21, 233 (1989).
Kozlowski, *J. Chromatogr.*, 318 (1985), 211–219.
Loubinoux et al., *Tetrahedron Letters*, 3951–3954, (1977).
Meunier, *J. Organometal. Chem.* 204 (1981), 345–346.
Rolla, *J. Org. Chem.*, 46, 3909–3911, (1981).
Stojkovski et al., *J. Chem. Tech. Biotechnol.* (1990), 51, 407–417.
Stojkovski et al., *J. Chem. Tech. Biotechnol.* (1991), 51, 419–431.
Tabaei et al., *Tetrahedron Letters*, 2727–2730, (1991).
Waid, "*PCBs and the Environment*", vol. II, 78, CRC Press, Boca Raton, Florida, 1968.

*Primary Examiner*—Joseph McKane
*Attorney, Agent, or Firm*—Mathews, Woodbridge & Collins

[57] ABSTRACT

Nitrogen-containing substituents of aliphatic or aromatic compounds can be reduced by treatment with a reagent comprising (i) at least one complex of a transition metal of group 4 or 5 with a multidentate or unidentate organic or inorganic ligand and (ii) a reducing agent. The reaction is conducted optionally in the presence of an aliphatic or aromatic amine, and/or in the presence of an inert organic solvent.

11 Claims, No Drawings

PROCESS FOR REDUCING ORGANIC POLLUTANTS

CROSS-REFERENCE TO RELATED APPLICATION

This is a continuation-in-part of Ser. No. 08/211,983 filed Aug. 15, 1994 now U.S. Pat. No. 5,608,138, the disclosure of which is incorporated in its entirety herein by reference.

BACKGROUND OF THE INVENTION

In Ser. No. 08/211,983 a process is described for the reduction of the chlorine content of polychlorinated hydrocarbons such as, for example, polychlorinated benzene and polychlorinated biphenyls. The process utilizes a reagent comprising (i) at least one complex of a transition metal of group 4 or 5 with a multidentate or unidentate organic or inorganic ligand and (ii) a reducing agent such as a hydridoborate. Typical of the first component is bis-($\eta^5$-cyclopentadienyl)titanium dichloride (titanocene dichloride) while sodium tetrahydridoborate is representative of the latter.

Various methods are employed in reducing nitrogen-containing substituents on aliphatic and aromatic compounds to amines. For example, the reduction of nitro substituents to amines involves reducing agents such as iron, zinc, or tin with acid; hydrogen with a catalyst such as platinum, palladium, or nickel; hydrogen with a catalyst; and sulfides.

Nitroso substituents and hydroxylamines can be reduced to amines by the same reagents which reduce nitro compounds. N-Nitroso compounds are similarly reduced to hydrazines. Azo, azoxy, and hydrazo substituents can be reduced to amines using metals, notably zinc, and acids, and sodium hydrosulfate as reducing agents. Diborane reduces azo substituents to amines.

Nitro substituents have been reduced to intermediates within the sequence, such as azoxy, with sodium arsenite, sodium ethoxide, glucose, and potassium borofluoride. The most common reducing agents for reducing nitro substituents to azo compounds are lithium aluminum hydride, and zinc and alkali. Other intermediate substituents within the sequence, such as nitroso, are reduced to azo compounds with lithium aluminum hydride as well. Zinc and sodium are the most common agents used in reducing nitro substituents to hydrazo compounds. Nitro substituents have also been reduced to hydrazo compounds electrolytically, or with lithium aluminum hydride mixed with a metal chloride such as titanium tetrachloride or vanadium trichloride, or hydrazine hydrate and Raney nickel.

On aliphatic compounds, lithium aluminum hydride reduces nitro substituents to amines, but nitro substituents on aromatic compounds are reduced to azo compounds. Lithium aluminum hydride does not generally reduce azo compounds (these are the products from lithium aluminum hydride reduction of nitro compounds), but these substituents can be reduced to hydrazo compounds by catalytic hydrogenation.

Most metal hydrides, such as sodium borohydride, reduce nitro substituents on aromatic compounds to azo and azoxy compounds, leaving the aromatic ring intact.

DETAILED DESCRIPTION

The present process is based on the discovery that nitrogen-containing substituents on aliphatic or aromatic compounds are reduced from an oxidative state higher than that of a primary amine to a lower oxidative state. The resulting compounds are readily converted into biodegradable amines upon hydrolysis.

The first component will contain a substantially nontoxic transition metal of Group 4 or 5 (IVa or Va) and will form a complex with multidentate and unidentate organic and inorganic ligands. Particularly preferred transition metals are titanium and zirconium. Preferred ligands include benzoates, chlorides, cyclopentadienides, substituted cyclopentadienides, indenides, substituted indenides, salens, porphyrins, tris(pyrazolyl) borates, poly(alkylaminos), poly(thioalkyls), and mixtures thereof. One highly effective subclass are the organometallic complexes of titanium and zirconium such as bis-($\eta^5$-cyclopentadienyl)titanium dichloride, bis-($\eta^5$-cyclopentadienyl)zirconium dichloride, $\eta^5$-cyclopentadienyl zirconium trichloride, and $\eta^5$-cyclopentadienyltitanium trichloride. Particularly useful in view of its currently relatively low cost and performance is bis-($\eta^5$-cyclopentadienyl)titanium dichloride, also known as titanocene dichloride.

The nitrogen containing substituents which are reduced by the process are nitro, nitroso, hydroxylamino, azo, azoxy, hydrazo, and the like.

Compounds with nitrogen containing substituents reduced by the process include highly explosive pollutants such as 2,4,6-tri-nitrotoluene, 1,3,5,7-tetranitrooctahydro-1,3,5,7-tetrazocine, hexahydro-1,3,5-trinitro-1,3,5-triazine, 2,4,6-trinitrophenol or glyceryl nitrate.

Nitrogen containing substituents on aliphatic or aromatic compounds are reduced in the process. The metal-catalyzed reduction leads to easily biodegradable organic products. Subjecting the reduced products of the reaction to hydrolysis forms titanium dioxide and borate by-products.

The process is effected in a single step. Nitrogen-containing substituents on compounds can be rapidly reduced to primary amines using the present system. Azobenzene is rapidly reduced to aniline. Diphenylhydrazine is even more rapidly reduced to aniline under the recited catalytic conditions. Intermediate compounds within the reduction sequence having nitrogen-containing substituents such as nitroso, hydroxylamino, azoxy, azo, and hydrazo species are also reduced by the catalyst system.

Addition of an amine to the reaction is optional, since the nitrogen inherently present in the nitrogen-containing substituents activates the metal complex.

When added, the additional amine can be any aliphatic amine such as trimethylamine, triethylamine, dimethylethylamine, etc., an aromatic additive amine such as N,N-dimethylaniline, N,N-dimethylnaphthylamine, etc., or an aromatic or nonaromatic heterocyclic amine such as pyridine, 1-methylimidazole, quinoline, piperidine, etc. Although primary and secondary amines can be employed, tertiary amines are preferred. Generally, a molar excess of the amine is employed.

The reaction can be conducted in a variety of inert organic solvents such as diglyme, triglyme, bis-(2-ethoxyethyl)ether, tetrahydrofuran, dimethylsulfoxide, ethylene glycol dimethyl ether and the like. Particularly preferred are ethers such as diglyme. In addition, an active solvent useful in the process is dimethylformamide.

Optionally a phase-transfer agent can be added to assist in dissolution of the reactants, particularly the hydridoborate. Typical of these are the methyltri($C_8$–$C_{10}$alkyl)ammonium chlorides.

Reaction times will depend on the reactants and temperature. The reaction thus can be conducted at temperatures of from about 50° C. to about 150° C. Preferably, the reaction is conducted at temperatures of 120° C. to about 130° C. Reduction of azobenzene at 125° C. is substantially complete in about one hour. Hydrazobenzene, when subjected to the identical temperature conditions, is reduced to azobenzene in about 30 minutes. In contrast, 2-(diethylamino)azobenzene takes longer to be reduced than azobenzene. Nitrobenzene is reduced to a mixture of aniline and azobenzene after about thirty minutes at 125° C. The resulting azobenzene can then be further reduced to aniline. The degree of reduction can be monitored using conventional analytical techniques such as gas chromatography.

In a further embodiment, the process reduces double bonds in polynuclear aromatic hydrocarbons from a higher oxidative state to a lower oxidative state. The resulting compounds are more readily biodegradable.

In the reduction of polychlorinated hydrocarbons, the reaction was driven overall by the removal of a halide group. However, certain polynuclear aromatic compounds, such as, for example, anthracene and napthacene, do not have substituent groups such as these. When reducing polynuclear aromatic hydrocarbons, preferably a proton source, such as aliphatic alcohols having a pKa of about 16 to 18, including methanol, ethanol, n-propyl alcohol, isopropyl alcohol, n-butyl alcohol, sec-butyl alcohol, isobutyl alcohol, and tert-butyl alcohol is added to the reaction. Of these, tert-butyl alcohol is preferred.

Since it has been found that titanocene dichloride and sodium tetrahydridoborate are stable to mildly acidic alcohols such as tert-butanol, polynuclear aromatic compounds can be reduced under relatively mild acidic conditions using the catalyst reagent.

Polynuclear aromatic hydrocarbons reduced by the process include anthracene, phenanthracene, napthacene, fluorene, pyrene, benzpyrene, chrysene, acenaphthene, and the like.

Optionally, an amine is added to the reaction in reducing polynuclear aromatic hydrocarbons. The optionally added amines employed in the reaction are those described previously.

The products resulting from the reduction of polynuclear aromatic hydrocarbons include dihydro and tetrahydro species, such as dihydroanthracene and tetrahydronaphthalene.

The following examples will serve to further typify the nature of the invention but should not be construed as a limitation on the scope thereof which is defined solely by the appended claims.

EXAMPLE 1

Two hundred fifty milligrams of titanocene dichloride (1.0 mmol), 1.24 grams of sodium tetrahydridoborate (0.033 mmol) and 15 mL of diethylene glycol dimethyl ether are heated in a reaction vessel at 125° C. In a separate reaction vessel, 0.99 grams of azobenzene (0.005 mmol) and 2.63 milliliters of pyridine are dissolved in 10 mL of diethylene glycol dimethyl ether. Thereafter, the separate solutions are combined and heated at 125° C. One milliliter aliquots are quenched with water, extracted with diethyl ether, purified by passing through a short column of silica gel, and subjected to gas chromatography analysis. The results of the analysis show that reduction to aniline occurs in approximately one hour.

EXAMPLE 2

Two hundred fifty milligrams of titanocene dichloride (1.0 mmol) and 1.24 grams of sodium tetrahydridoborate (0.033 mol) are heated in a reaction vessel at 125° C. with fifteen milliliters of diethylene glycol dimethyl ether. In a separate vessel, 1.32 grams of 4-(diethylamino)azobenzene (0.005 mmol) and 2.63 milliliters of pyridine are dissolved in ten milliliters of diethylene glycol dimethyl ether. The two solutions are combined and the resulting reaction mixture is heated at 125° C. One milliliter aliquots are quenched with water, extracted with diethyl ether, purified by passing through a short column of silica gel and subjected to gas chromatography analysis. Reduction of 4-(diethylamino)azobenzene results in a mixture of aniline and 4-(diethylamino)aniline.

EXAMPLE 3

One hundred twenty-five milligrams of titanocene dichloride (0.5 mmol), 0.62 grams of sodium tetrahydridoborate (0.016 mol), 0.50 grams of 1,2-diphenylhydrazine (0.003 mol), and 1.32 mL of pyridine are dissolved in 10 mL of diethylene glycol dimethyl ether and introduced into a reaction vessel. The reaction mixture is heated at 125° C. for approximately thirty minutes. One milliliter aliquots are withdrawn and quenched with water, extracted with diethyl ether, purified by passing through a short column of silica gel and analyzed by gas chromatography to show reduction to aniline.

EXAMPLE 4

Two hundred fifty milligrams of titanocene dichloride (1.0 mmol), 1.24 grams of sodium tetrahydridoborate (0.033 mmol), and fifteen milliliters of diethylene glycol dimethyl ether are introduced into a reaction vessel and heated at 125° C. A solution of 0.98 grams of nitrobenzene (0.008 mmol) and 2.6 mL of pyridine dissolved in 10 mL of diethylene glycol dimethyl ether is added to the mixture. The resulting reaction mixture is heated at 125° C. One milliliter aliquots are quenched with water, extracted with diethyl ether, purified by passing through a short column of silica gel and subjected to gas chromatography analysis. Nitrobenzene was reduced to a mixture of aniline and azobenzene in about 30 minutes. The remaining azobenzene was further reduced to aniline by following the procedure of Example 2.

EXAMPLE 5

In a suitable reaction vessel, 1.24 grams of sodium borohydride (0.033 mmol) and 15 milliliters of diethylene glycol dimethyl ether are heated at 125° C. In a separate reaction vessel, 0.99 grams of azobenzene (0.005 mmol) and 2.63 milliliters of pyridine are dissolved in 10 mL of diethylene glycol dimethyl ether. The two solutions are combined and heated at 125° C. One milliliter aliquots quenched with water are extracted with diethyl ether and purified by passing through a short column of silica gel. The results of the gas chromatography analysis show that after twenty-four hours, more than 80% of the starting material remains.

EXAMPLE 6

In a reaction vessel, 26.6 mg of titanocene dichloride (0.107 mmol) and 20.3 mg of sodium tetrahydridoborate (0.537 mmol) are dissolved in 10 mL of diethylene glycol dimethyl ether. A solution of 40 mg of anthracene (0.225 mmol), 0.04 mL of pyridine, and 16.6 mg of tert-butyl alcohol (0.224 mmol) is added. The reaction mixture is heated at 125° C. One milliliter aliquots are hydrolyzed, extracted with diethyl ether, purified by passing through a short column of silica gel, and analyzed by gas chromatography to show complete conversion to 9,10-dihydroanthracene as the major product, and 1,2- and 1,4-dihydroanthracene as the minor products.

What is claimed is:

1. In the process of reducing a nitrogen-containing substituent in an aliphatic or aromatic compound in which said substituent is at an oxidative state higher than that of a primary amine, to a nitrogen-containing substituent having a lower oxidative state, the improvement which comprises treating said compound in the presence of a reagent comprising:

(i) at least one complex of a transition metal of group 4 or 5 with a multidentate or unidentate organic or inorganic ligand; and (ii) a reducing agent.

2. The method of claim 1 wherein said ligand complex is cyclopentadienide.

3. The process according to claim 1 wherein the complex is a titanium or zirconium complex.

4. The process according to claim 3 wherein the reducing agent is a hydridoborate or a polyhydridoborate.

5. The process according to claim 4 wherein the reducing agent is an alkali metal or metal chelate thereof, or ammonium salt of a tetrahydridoborate, thiocyanatotrihydridoborate, cyanotrihydridoborate, acyloxytrihydridoborate, octahydridotrihydridoborate, trialkylhydridoborate, acetanilidetrihydridoborate, trialkoxyhydridoborate.

6. The process according to claim 1 wherein the reduction is conducted in the presence of an aliphatic or aromatic amine.

7. The process according to claim 6 wherein the amine is trimethylamine, triethylamine, dimethylethylamine, N,N-dimethylaniline, N,N-dimethylnaphthylamine, pyridine, 1-methylimidazole, quinoline, or piperidine.

8. The process according to claim 6 wherein the reduction is conducted in the presence of an inert organic solvent.

9. The process according to claim 8 wherein the inert organic solvent is diglyme, triglyme, bis-(2-ethoxyethyl)-ether, tetrahydrofuran, dimethylsulfoxide, or ethylene glycol dimethyl ether.

10. The process according to claim 1 wherein the complex is bis-($\eta^5$-cyclopentadienyl)titanium dichloride and the reducing agent is sodium tetrahydridoborate.

11. The process according to claim 1 wherein the aliphatic or aromatic compounds are trinitrotoluene, trinitrophenol, glyceryl nitrate, 1,3,5,7-tetranitrooctahydro-1,3,5,7-tetrazocine, or hexahydro-1,3,5-trinitro-1,3,5-triazine.

* * * * *